United States Patent [19]

Manara et al.

[11] 4,302,597

[45] Nov. 24, 1981

[54] METHOD FOR THE HYDRATION OF ACRYLONITRILE TO ACRYLAMIDE

[75] Inventors: Giovanni Manara; Vittorio Fattore; Bruno Notari, all of San Donato Milanese, Italy

[73] Assignee: Snamprogetti, S.p.A., Milan, Italy

[21] Appl. No.: 62,618

[22] Filed: Aug. 1, 1979

Related U.S. Application Data

[63] Continuation of Ser. No. 878,775, Feb. 17, 1978, abandoned, which is a continuation of Ser. No. 731,991, Oct. 13, 1976, abandoned.

[30] Foreign Application Priority Data

Oct. 17, 1975 [IT] Italy .............................. 28384 A/75

[51] Int. Cl.$^3$ .......................................... C07C 103/133
[52] U.S. Cl. ..................................... 564/127; 564/128
[58] Field of Search .................. 260/561 N; 252/474, 252/477 Q; 75/0.5 A; 564/127, 128

[56] References Cited

U.S. PATENT DOCUMENTS

| | | | |
|---|---|---|---|
| 3,032,515 | 5/1962 | Hinsvark | 252/477 Q UX |
| 3,188,230 | 6/1965 | Bakish et al. | 427/252 X |
| 3,997,606 | 12/1976 | Kane | 260/561 N |
| 4,048,226 | 9/1977 | Barber et al. | 260/561 N |

FOREIGN PATENT DOCUMENTS 828973  10/1956  United Kingdom .

*Primary Examiner*—Helen M. S. Sneed
*Attorney, Agent, or Firm*—Morgan, Finnegan, Pine, Foley & Lee

[57] ABSTRACT

In the reaction of conversion of nitriles to amides, more particularly, but not exclusively, acrylonitrile to acrylamide, the improvement consisting in the adoption, as a catalyst, of a copper-based catalyst which is prepared by reacting an organic copper chelate with aluminum-alkyl and/or an aluminum hydride. Higher yields and higher selectivity are obtained over the usual copper-based catalysts.

4 Claims, No Drawings

METHOD FOR THE HYDRATION OF ACRYLONITRILE TO ACRYLAMIDE

This is a continuation of application Ser. No. 878,775 filed Feb. 17, 1978, now abandoned which in turn is a continuation of application Ser. No. 731,991 filed on Oct. 13, 1976, now abandoned.

This invention relates to a method for the preparation of amides by hydration of nitriles in the presence of a heterogeneous catalyst solid. More particularly, the invention relates to the hydration of acrylonitrile to acrylamide.

It is known that amides, and especially acrylamide, can be used as reinforcing agents for paper, soil-solidification agents and fiber-treatment agents.

Their production on an industrial scale, however, is costly still nowadays, or is complicated by special requirements which are a result of the nature of the reactions, so that the endeavours are understandable, which are directed continuously to improve the preparation methods, It is likewise known that catalysts for the hydration of nitriles can be constituted of reduced oxides of copper or other reduced metals (U.S. Pat. No. 3,597,481), or by metallic copper, Raney copper and others as disclosed by the Italian Pat. No. 912,603 and the British Pat. No. 1,353,302. However, the results achieved heretofore with said methods are not an evidence of a high activity.

The subject matter of the present invention is a method for the catalytic hydration of nitriles to amides which provides a high conversion rate and a high selectivity. A second aspect of the present invention is an improved catalyst for the hydrolysis of a nitrile to its corresponding amide. More particularly, the subject-matter of the present invention is a method for the catalytic hydration of acrylonitrile which affords a high conversion and a high selectivity.

According to the present invention, a method has been envisaged for the hydration of nitriles to amides, the method comprising the step of causing such a reaction to take place in the presence of an improved copper-based catalyst which is obtained by reacting a copper compound with a reducing agent such as an aluminum-alkyl and/or hydride, which is possibly partially substituted. In the descriptive portion of this specification, reference will always be had to derivatives of aluminum but it should be borne in mind that other derivatives, such as magnesium alkyls and hydrides behave in a similar manner. In the ensuing description reference will be made to the copper-based catalyst so prepared, also with the wording "active copper". The reaction for preparing the catalyst is conducted preferably in an inert atmosphere, between an appropriate copper compound, as dispersed in a hydrocarbonaceous solvent, and the aluminum compound, which can be dissolved, in turn, in a hydrocarbonaceous solvent. The copper compounds which are adapted to this purpose are a few organic derivatives, and preferred among these are, the complexes formed by copper with a few chelation agents, such as for example: acetylacetone, salicyl aldehyde, benzoyl acetone, dibenzoyl methane, furoyl acetone, 2-furoyl benzoylmethane, dimethylglyoxime, ethylmethylglyoxal, diacetyl.

As the organic solvents alicyclic hydrocarbons, aliphatic or aromatic hydrocarbons, preferably with a number of carbon atoms below 15, such as for example n-hexane, n-heptane, cyclohexane, benzene, can be used. The reduction reaction of the copper derivative can be made at temperatures in the range between 10° C. and 100° C. consistently with the particular aluminum compound, the boiling point temperature of the solvent, the concentration of the latter in the organic solution and the higher or lower reaction velocity expected. Usually, the working pressure is atmospheric but it is possible to carry out the reaction also under a subatmospheric, or a superatmospheric pressure. On completion of the reduction step, and still in an inert atmosphere, the solvent is stripped, as is the excess of reducing substance, prior to transferring the active copper so prepared into the reaction vessel for the hydrolysis of the nitriles.

The hydration method can be carried out over wide range of operating conditions.

According to the invention, the method is preferably carried out under atmospheric pressure, but gives satisfactory results also under subatmospheric and superatmospheric pressures as well. The reaction temperature can be selected between 20° C. and 200° C., although working temperatures of from 50° C. to 150° C. are preferred. The concentration of the nitrile can be varied within a wide range and homogeneous, as well as heterogeneous, solutions can equally well be treated. The ratio of water to nitrile in the reaction mixture can be varied from 1 to 30 mols of water per mol of nitrile. The preferred nitrile concentrations range from 5% to 50% by weight. The pH is not a critical parameter, though it is preferred to operate in the pH range from 1 to 7. The hydration reaction can take place also with different nitriles other than the exemplified acrylonitrile, such as for example, with benzonitrile, acetonitrile, methacrylonitrile, propionitrile, the same advantages as illustrated for acrylonitrile being likewise obtained. The ratio between the amount of catalyst and the nitrile solution with which it is put into contact is not critical and can be varied over a wide range. The preferred weight ratios between the solution and the catalyst, in order that the advantages of this invention may be better achieved, are between 50 to 1 and 2 to 1.

Active copper can be used as such or it can be suppported by alumina, silica, activated carbon or other supports having a high specific surface.

The solid catalyst as used in the present invention can be employed both in continuous and batch runs. The catalyst can also be a fixed bed through which the reactants are caused to flow in the form of a solution or an emulsion, aqueous or organic, with a certain mutual solubility. On the other hand, the catalyst can be maintained in suspension in the liquid phase by stirring or otherwise.

In continuous processes, the volume in liters of reaction mixture, as measured at room temperature, which is caused to flow during one hour over each liter of catalyst, can be varied between 1 and 150.

The reaction products are appropriately separated from the aqueous mixture according to the conventional methods known to those skilled in the art, such as evaporation and recrystallization. The catalyst can either be separated by centrifugation or filtered off in the batch processes. The unreacted nitrile can be separated and recycled according to conventional techniques.

The ensuing examples illustrate a few of the preferred possible embodiments of the invention, together with a comparison of the results which can be achieved according to the conventional art.

The detailed data set forth herein are intended to illustrate the applicability of the method of the present invention, but are not to be construed as limitations thereto.

EXAMPLE 1

A catalyst has been prepared, which is composed of active copper obtained by reducing with aluminum triisobutyl the copper acetyl acetonate. There are slurried in 1 liter of anhydrous nor.hexane, 52.3 grams of copper acetyl acetonate and there are added dropwise 5 liters of a 20% (volume to volume) of Al (iso $C_4H_9$)$_3$ in nor.hexane, while keeping the reaction vessel vigorously stirred and under a stream of anhydrous nitrogen. The liquid is separated by decantation, the excess of Al (iso $C_4H_9$)$_3$ is washed with nor.hexane and the thusly obtained catalyst is used for the hydration reaction of acrylonitrile to acrylamide.

In a pressure reactor having the capacity of 500 mls maintained under an anhydrous nitrogen atmosphere, there are introduced 50 grams of acrylonitrile, 100 grams of water and 10 grams of active copper.

The reactor is heated to 110° C. and the reaction mixture is maintained vigorously stirred.

The analysis of the reaction products is effected by gas-chromatographic methods. After 5 hours, there is obtained a conversion of the acrylonitrile which is higher than 99% since the by-products cannot be analytically evaluated as to their quantity.

EXAMPLE 2

Under the same conditions as in Example 1, there are reacted 100 grams of acrylonitrile, 100 grams of water and 10 grams of copper catalyst, as prepared according to the indications of Example 1.

After 8 hours, there is obtained a conversion of the acrylonitrile higher than 99% and the selectivity to acrylamide is 99% at the gas-chromatographic analysis.

EXAMPLE 3

There are slurried in 250 mls of anhydrous nor.hexane, 5.23 grams of copper acetylacetonate and there is added dropwise a solution of 150 grams of polyiminoalane (prepared according to what has been disclosed in U.S. Pat. No. 4,022,809) in 1,500 mls of nor.hexane, operating at room temperature under a nitrogen stream. The liquid is decanted, the copper is washed with nor.-hexane and the thusly obtained active copper is used for the catalytic hydration of the acrylonitrile to acrylamide.

The working temperature is 70° C. and the reaction mixture is kept stirred under a nitrogen stream, reacting 20 parts of acrylonitrile and 45 parts of water in the presence of 6 parts of active copper.

The gaschromatographic analysis indicates a conversion of 75% within a period of 4 hours, with an acrylamide selectivity as high as 99%. After 6 hours, the conversion attains 90%, still with a selectivity of 99%.

EXAMPLE 4

The catalyst used in Example 3 is separated by filtration from the reaction products, washed with water and reused for the hydration of acrylonitrile to acrylamide, by operating under the same conditions and the same amounts of reactants as in the previous Example.

The conversion of acrylonitrile, as evaluated by the gaschromatographic way, attains 75% after 4 hours, with a selectivity in acrylamide as high as 99%, thus showing that the catalyst did not undergo any deactivation in use.

EXAMPLE 5

200 Grams of anhydrous gamma-$Al_2O_3$ are impregnated with an aqueous solution of cupric chloride, so that the copper contents of the catalyst is 10%.

The reaction is carried out in an aqueous medium with 90 grams of potassium acetylacetonate, washing until the chloride ion reaction is over and drying in a vacuo at 60° C.

The thusly obtained alumina supported copper acetylacetonate is reduced with a solution of Al (iso $C_4H_9$)$_3$ as indicated in Example 1.

The pressurized reactor of Example 1 is charged with 50 grams of acrylonitrile, 100 grams of water and 40 grams of catalyst, equivalent to 4 grams of reduced copper. The reactor is heated to 120° C. with stirring and stirring is continuously maintained.

After 8 hours a 40% conversion of acrylonitrile is obtained, with an acrylamide selectivity as high as 95%.

EXAMPLE 6

The pressurized reactor of Example 1 is maintained under an anhydrous nitrogen stream and is charged with 7 grams of acrylonitrile, 93 grams of water and 20 grams of active copper as prepared according to Example 1.

The reactor is heated to 100° C. and the reaction mixture is kept stirred during 30 minutes.

The gaschromatographic analysis of the reaction products shows that 99% of acrylonitrile has been converted to acrylamide, with a selectivity of 99%.

EXAMPLE 7

With the same procedure of Example 1 a copper-based catalyst is prepared by substituting, for the copper acetylacetonate, a corresponding quantity of monohydrous cupric acetate.

10 Grams of the thusly obtained copper-based catalyst are introduced, under an anhydrous nitrogen atmosphere in the reactor of Example 1, together with 50 grams of acrylonitrile and 100 grams of water.

The reaction mixture is kept stirred constantly for 5 hours and a conversion of acrylonitrile of 40% is obtained, with an acrylamide selectivity of 95%. By comparing these data with the results as obtained under the same conditions with the active copper of Example 1, which was prepared with copper acetylacetonate, it is apparent that a copper-based catalyst is obtained, which is much more active, if one uses, instead of a common copper salt, one of the chelates as suggested by the present invention, such as for example copper acetylacetonate.

EXAMPLE 8

A copper-Raney catalyst is prepared by reacting at 0° C. and with a vigorous stirring, the Devarda alloy with an aqueous solution of sodium hydroxide. After heating overnight at 70° C., the mixture was washed with a fresh NaOH solution, then with water until the alkalies have been discharged, then with 95% ethanol and then with abs.ethanol, The thusly prepared catalyst is maintained under abs. alcohol until the time of its use comes.

A comparison test is carried out, between the copper-Raney and the active copper as prepared according to the present invention with the procedure as in Example 1 hereof.

In two reactors, kept stirred under an anhydrous nitrogen stream, there are reacted at 70° C.:20 parts of acrylonitrile, 45 parts of water, and, respectively, 3 parts of copper-Raney in the first reactor, and 2 parts of active copper in the second one.

The reaction mixture is periodically analysed by the gaschromatographic method so as to follow the progress in time of the conversion of acrylonitrile to acrylamide.

The results are tabulated in TABLE 1, wherein it is clearly shown that the active copper as prepared according to the present invention, though contained in lesser amounts than in the copper-Raney, is much more active, since it attains a complete conversion of the acrylonitrile within a period of time which is considerably shorter. The final selectivity was 99% for both catalysts.

TABLE 1

CATALYTIC HYDRATION OF ACRYLONITRILE TO ACRYLAMIDE.-
Temperature: 70° C.: Atmospherical pressure

| TIME, hours | % CONVERSION OF ACRYLONITRILE TO ACRYLAMIDE | |
|---|---|---|
| | Copper Raney catalyst | Active copper catalyst |
| 1 | 8 | 20 |
| 3 | 20 | 37 |
| 5 | 30 | 50 |
| 7 | 40 | 60 |
| 9 | 52 | 68 |
| 11 | 60 | 75 |
| 13 | 65 | 90 |
| 15 | 72 | 99 |
| 17 | 80 | |
| 19 | 88 | |
| 24 | 97 | - |

EXAMPLE 9

In another comparative Example, 50 parts of water and 50 parts of acrylonitrile are reacted at 70° C. under a stream of anhydrous nitrogen and with stirring, respectively in the presence of 4 parts of copper-Raney and 4 parts of active copper as prepared according to the suggestions of the previous Example 8 hereof.

After a 2-hour reaction, the conversion of acrylonitrile to acrylamide, as determined by gaschromatographic analysis, was 27% in the case of the copper-Raney and 51% in the case of the active copper, with a selectivity of 96% in the former case, and of 99% in the latter. Also under these conditions, the superior performances of the active copper are self-explanatory.

EXAMPLE 10

By way of comparison, a copper-based catalyst is prepared, as obtained by adding a solution of 40 grams of pentahydrous cupric sulfate in 750 mls distilled water, to one liter of an aqueous solution which contained 8 grams of sodium borohydride and 7 grams of sodium hydroxide. During progress of the addition, and until hydrogen as evolved, the reaction vessel was cooled in an ice bath. The precipitate thus obtained is filtered off and then used for the hydration of acrylonitrile, which is carried out in the reactor of the previous Example 8.

The reaction is carried out during 30 minutes at 60° C. under a nitrogen stream, with 50 grams of water, 3 grams of acrylonitrile and, respectively, 10 grams of copper as obtained by reduction with sodium borohydride and 10 grams of active copper as prepared according to the procedure of Example 1.

The conversion of acrylonitrile to acrylamide, as measured by gaschromatographic analysis, is 52% in the case of the copper which had been reduced with sodium borohydride and of 81% in the case of the active copper, the selectivity being 97% in the former case, and 99% in the latter.

What we claim is:

1. A method for the hydration of acrylonitrile to acrylamide comprising the step of carrying out the reaction by starting with an aqueous reaction mixture in which the ratio of water to acrylonitrile is in the range of from 1 to 30 mols of water per mol of acrylonitrile, at a temperature in the range of from 20° C. to 200° C. and in the presence of a catalyst based on copper obtained by reacting an organic chelate of copper with an aluminum alkyl and/or hydride.

2. A method for the hydration of acrylonitrile to acrylamide as claimed in claim 1, wherein the reaction is carried out at a temperature in the range from 20° C. to 200° C.

3. A method for the hydration of acrylonitrile to acrylamide as claimed in claim 1, wherein the concentration of acrylonitrile is in the range of from 5% to 50% on a weight basis.

4. A method for the hydration of acrylonitrile as claimed in claim 1, wherein the reaction takes place at a ratio between a solution of the acrylonitrile and the catalyst which is in the range of from 50 to 1 and 2 to 1.

* * * * *